United States Patent [19]

Nordqvist et al.

[11] Patent Number: 4,575,371
[45] Date of Patent: Mar. 11, 1986

[54] URINARY CATHETER

[76] Inventors: Percy Nordqvist, Budskär, Särö, Sweden; Eric Hylerstedt, S:t Sigfridsg. 69, Göteborg, Sweden, 412 66

[21] Appl. No.: 738,509
[22] PCT Filed: Apr. 16, 1982
[86] PCT No.: PCT/SE82/00124
  § 371 Date: Dec. 13, 1982
  § 102(e) Date: Dec. 13, 1982
[87] PCT Pub. No.: WO82/03557
  PCT Pub. Date: Oct. 28, 1982
  (Under 37 CFR 1.47)

Related U.S. Application Data

[63] Continuation of Ser. No. 453,899, Dec. 13, 1982, abandoned.

[30] Foreign Application Priority Data

Apr. 16, 1981 [SE] Sweden .............................. 8102467

[51] Int. Cl.⁴ ........................................... A61M 25/00
[52] U.S. Cl. ...................................... 604/96; 604/100
[58] Field of Search .................... 604/96-103

[56] References Cited

U.S. PATENT DOCUMENTS

| | | |
|---|---|---|
| 1,922,084 | 8/1933 | Gerow . |
| 2,173,527 | 9/1939 | Agayoff .............................. 604/96 |
| 3,438,375 | 4/1969 | Ericson .............................. 604/98 |
| 3,746,003 | 7/1973 | Blake et al. ........................ 604/100 |
| 3,924,634 | 12/1975 | Taylor et al. ...................... 604/100 |
| 4,022,216 | 5/1977 | Stevens .............................. 604/101 |
| 4,148,319 | 7/1979 | Kasper et al. ..................... 604/96 |
| 4,430,076 | 2/1984 | Harris ................................. 604/96 |

FOREIGN PATENT DOCUMENTS 2818119 11/1979 Fed. Rep. of Germany ........ 604/96
2089844 1/1972 France .

Primary Examiner—Dalton L. Truluck
Attorney, Agent, or Firm—Holman & Stern

[57] ABSTRACT

The present invention discloses a urinary catheter with a retention member in the form of an expandable balloon. The expandable balloon is arranged below the inlet opening and so designed that in its inflated condition a portion projects forward past the catheter tip at some distance from the inlet opening. The unique design of the catheter prevents contact between the wall of the urinary bladder and the catheter tip thereby avoiding infection and traumatization of the tissues.

4 Claims, 5 Drawing Figures

FIG 3
FIG 4
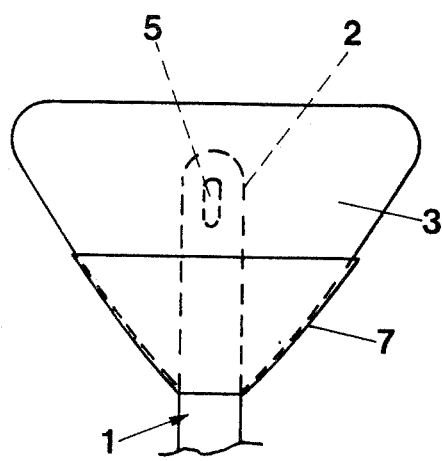
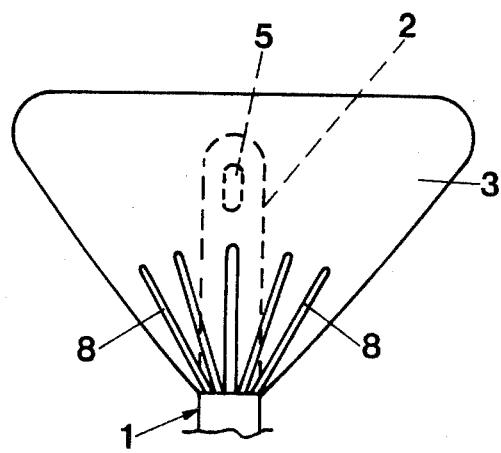
FIG 5
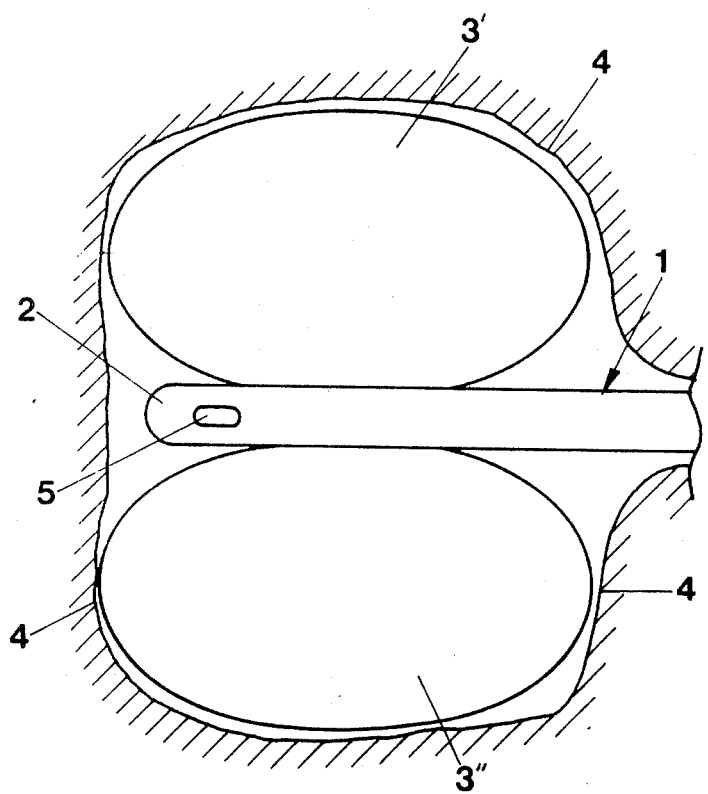

URINARY CATHETER

This is a continuation of application Ser. No. 453,899, filed Dec. 13, 1982, now abandoned.

A urinary catheter comprising an elongated member for transporting urine through urethra and provided with a pointed end enabling insertion of the catheter through urethra and having at least one radial inlet opening for the urine close to said pointed end and a retention member in the form of an expandable balloon arranged at said end portion below said inlet opening as seen in the position of use of the catheter in the urinary bladder and intended to when located in the urinary bladder of the user extend outside said member in the radial direction thereof and retain the catheter in position.

Patients who are urinary incontinent or have urine retention are usually treated with so called balloon catheters of the above mentioned kind.

A considerable disadvantage of conventional balloon catheters is that the catheter tip, which projects 1-2 cm in front of the expanded balloon, often causes irritating injuries in the area where the catheter tip contacts the mucous membrane of the urinary bladder. The catheter tip has to be made fairly hard and pointed for enabling its insertion through the often narrow urethra.

Injuries of this kind have been commonly known by urologists, who have noticed them at cystoscopies.

The first known systematic investigation of injuries occuring in connection with the use of urinary catheters is to be found in the article "Catheter-Induced Haemorragic Pseudopolyps of the Urinary Bladder" in JAMA 198, 196, 1965. The haemorrhages and polyps noticed are ascribed to the fact that a negative pressure can arise in the catheter system. The mucous membrane can then be sucked into the inlet openings in the catheter tip and be injured. These injuries then allow possible growth of microorganisms. In order to improve catheter treatment for the patients and prevent severe infections caused by these injuries many modifications have been tried.

Catheters have been treated with antibacterial substances, they have been coated with hydrophilic polymers and daily installations with antibacterial lubricants have been made without any obvious effect.

It has also been proposed to avoid the mucous membrane being sucked into the holes at the catheter tip, by constructing a catheter with a ventilating system, which balances the negative pressure.

It has been reported that with such systems no significant reduction of the rate of bacterial colonization could however be noticed (Finkelberg Z & Kunin C. M. JAMA 207, 1657, 1969). Neither could there be noticed any significant difference between ventilated drainage and conventional drainage in a very extensive examination of 506 patients and concerning admixture of blood into the urine during catheter treatment (Monson T. P. & al J. Urol. 117, 216, 1970).

Besides that no significant positive effects have been noticed with such systems, they are comparatively complicated and expensive as compared to conventional systems.

An examination by Axelsson et al, published in Acta Path, *Microbiol. Scand.*, volume II, p. 283-287, has confirmed that it is the catheter tip, which lies freely in the urinary bladder, which causes the injuries of the mucous membrane. At this examination it has by means of scanning electron microscope been shown that conventional catheter tips have such a configuration that the mucous membrane is injured when contacting the tip. At a newly published examination by Ekelund P. et al, Acta Path, *Microbiol. Scand.* Sect. A, 87:179-184, 1979 it is finally established that injuries of the urinary bladder cause the disease Polyposis cysta and that the contact of the catheter tip with the mucous membrane is the main cause. These changes are according to the examination found at about 75% of the catheter users after one month.

In the U.S. Pat. No 3,438,375 there is described different catheter shapes, with which one tries to avoid one of the drawbacks of the catheters commonly used: sucking of the mucous membrane into the inlet opening when the urinary bladder is drained through the catheter. As long as the catheter is closed and there is urine in the bladder, it is however at first hand the tip of the catheter that hurts the mucous membrane. In said patent it is also suggested to arrange the balloon at the front end of the catheter (FIGS. 4a, 14, 22), i.e. the catheter is not in this case provided with a tip.

In order to enable the insertion of a catheter through especially a male urethra it is required that the front end of the catheter is shaped in a way to admit insertion through narrow passages. To coax a catheter with an almost blunt front end and besides provided with an empty balloon envelope through the sharp turn below the pelvis floor muscles and through the narrow passage at the prostate gland would probably be impossible.

In the U.S. Pat. Nos. 1,922,084 and 3,954,110 there are described catheters, in which the expandable balloon is arranged at the catheter tip and by that prevents that the tip irritates the mucous membrane of the urinary bladder. This however involves certain drawbacks.

The inflow to the urinary bladder from the kidneys comes by way of the ureters, which end at the upper corner of frigonumis a way up (proximally) in the urinary bladder. A catheter drains the urinary bladder, at which the bladder wall closes round the balloon as soon as the urine no longer expands the bladder. If the draining hole is located below (distally) the balloon a continuous drainage cannot be used, which is the most common catheter treatment method.

Catheter treatment is used against urinary incontinence, the most frequent reason of which at least for women is a weak pelvis floor musculature. When a non-incontinent person urinates the muscles of the pelvis floor slacken, at which the distal part of the urinary bladder is reshaped to a "funnel". If the pelvis floor owing to high age or injury, e.g. in connection with child birth, does not have its normal muscle tonus this "funnel-shape" occurs at distal parts of the urinary bladder also when the patient does not want to urinate. A draining hole arranged below (distally) the balloon can therefore be located so far down in "the funnel" towards urethra that a satisfactory drainage is not possible.

The U.S. Pat. No. 2,677,375 discloses a catheter which has no tip which could hurt the mucous membrane. However the drainage hole can come into direct contact with the mucous membrane of the urinary bladder and thus at a negative pressure hurt this. Since this catheter also is flat at the end to be inserted into urethra the drainage hole has been provided with a cross of latex or rubber. In order to avoid the difficulty of passing through urethra at the pelvis floor bend and at the prostate gland a mandrin can be used at the insertion. This however means a complication.

The object of the present invention is to provide a catheter with which the above mentioned drawbacks in connection with the use of catheters are avoided, i.e. which simulataneously has a drainage hole protected by the balloon and a normally shaped catheter tip, which will not bump the mucous membrane of the urinary bladder when the balloon "floats" within a filled urinary bladder. The catheter hereinbefore described in the introduction is according to the invention characterized by the fact that said expandable balloon is so designed, that in expanded condition portions of the balloon project forwards past the catheter tip at some distance from the inlet opening and preventing contact between the mucous membrane of the urinary bladder and the catheter tip as well as the inlet opening.

The invention will now be further described with reference to some embodiments shown in the accompanying drawings.

FIGS. 3 and 4 show side views of somewhat modified embodiments of the urinary catheter according to FIG. 2, FIG. 5 shows schematically a further embodiment of the urinary catheter according to the invention placed in a urinary bladder.

In the drawings corresponding parts in the different figures have been denoted with the same numerals. Further only the front part of the urinary catheter, which is placed in the urinary bladder, is shown in the drawings.

Figure 1:
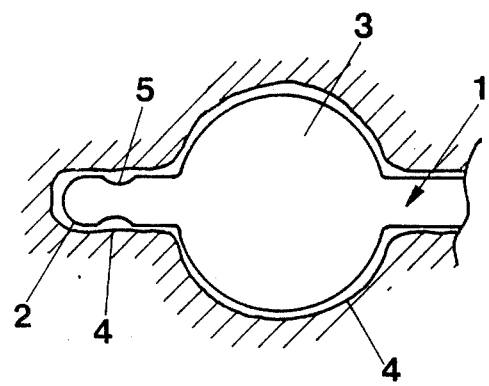
FIG. 1 shows schematically a conventional urinary catheter placed in the urinary bladder.

At the previously known catheter 1 according to FIG. 1 the hard and pointed catheter tip 2 projects in front of the expanded balloon 3.

When the urinary bladder, the walls of which are denoted with the numeral 4 in the drawing, is emptied from urine it is compressed by means of its muscles to the shape shown in FIG. 1. The musculature in the urinary bladder comprises three layers, the inner and outer of which extend in one plane and the intermediate circularly. The mucous membrane of the urinary bladder is fixed to the muscle wall of the urinary bladder. Especially the contraction of the circular muscle layer results in that the muscle wall with the mucous membrane is pressed against the catheter tip 2. Thus the tip will scrape against and irritate the mucous membrane of the urinary bladder.

When catheter users move or change position they often try to change the position of the catheter in the urinary bladder. The hard and pointed catheter tip 2 is then pressed hard against the mucous membrane of the urinary bladder, which thus can be seriously injured.

As can be seen from FIG. 1 wall portions of the emptied urinary bladder are located close to the inlet opening 5 for the urine. When a negative pressure arises in the catheter system said wall portions can be sucked into the holes and be hurt.

Figure 2:
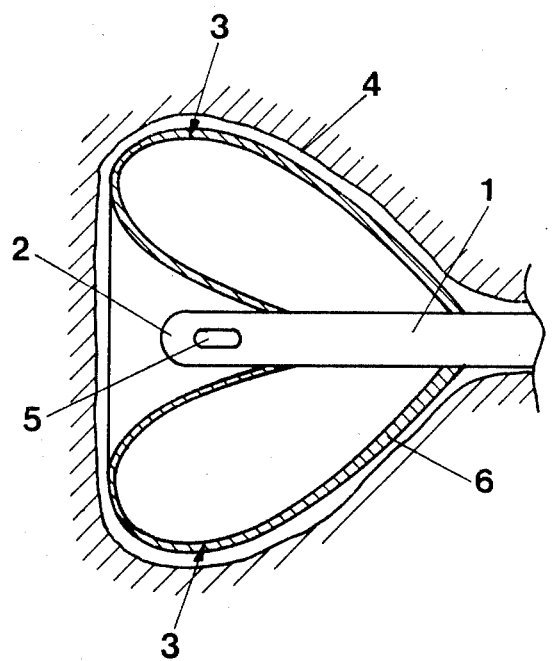
FIG. 2 shows schematically a first embodiment of the catheter according to the present invention placed in the urinary bladder.

In FIG. 2, which shows a catheter according to the invention, the expandable balloon has for the sake of clarity been shown in cross-section. In the embodiment shown in FIG. 2 of the catheter according to the invention the expandable balloon 3 has at the area 6 closest the mouth of urethra as seen in the position of use, been designed with a thicker wall as compared to the rest of the balloon. The expandable balloon will thus when being inflated expand in the direction obliquely forwards past the catheter tip, as is shown in FIG. 2.

An emptied urinary bladder adapts itself substantially to the shape of the expanded balloon. The muscle arrangement of the urinary bladder however prevents the muscle wall and the mucous membrane from being sucked towards the catheter opening 5, when this is placed at the centre of a bowl-shaped balloon.

There is however no risk at all that the mucous membrane could come into contact with the hard catheter tip. The fundus of the urinary bladder can simply not be sucked down into the balloon-bowl since the so called medial umbilicula ligament will prevent this (see Frank H. Netter "The Ciba Collection of Medical Illustrations", Vol. 6, p. 21, second printing N.Y. 1975).

A further advantage of the shape of the expanded balloon according to FIG. 2, is that the risk of injuries of the urethra is smaller than for conventional catheters if the catheter unintentionally and without the expanded balloon having been emptied is drawn out of the urinary bladder. The portion of the bowl-shaped balloon located round the tip can be bent somewhat towards the tip when the urethra presses against the balloon.

The embodiments of the urinary catheter according to the invention shown in FIGS. 3 and 4 in all essentials correspond to the embodiment of FIG. 2. Instead of making the wall of the expandable balloon 3 thicker in the area 6 than the rest of the balloon a resiliently stretchable tube 7 has according to the embodiment of FIG. 3 been applied over this area. In the embodiment shown in FIG. 4 the area 6 has instead of thicker wall portions been provided with reinforcing ridges 8. The tube 7 and the ridges 8 respectively give the same effect concerning the shape of the expanded balloon as the thicker wall portion according to FIG. 2.

The catheter according to FIG. 5 is provided with an expandable balloon comprising two chambers 3' and 3", which are arranged on opposite sides of the catheter tube and which in expanded condition project in front of the tip 2. In the embodiment according to FIG. 6 the balloon is arranged as close to the tip that no further arrangements are necessary for making portions of the balloon project in front of the catheter tip.

The invention is not limited to the above described embodiments, but a plurality modifications of are possible within the scope of the accompanying claims. As an example the bowl-shaped balloon can be provided by making different portions of the walls of the balloon of different materials with different extension properties.

Other types of reinforcing members than the ones shown with reference to FIG. 4 are, of course, possible.

We claim:

1. A urinary catheter comprising an elongated member for transporting urine through the urethra and provided with a point end enabling insertion of the catheter through the urethra and having at least one radial inlet opening close to said point end a retention member in the form of an expandable balloon arranged distally with respect to said inlet opening wherein the walls of the expandable balloon at a portion remote from the catheter tip being stiffer than the rest of the balloon, the opposite more flexible portion being arranged when inflated to expand obliquely forwards, so that the balloon assumes a bowl-like shape, the front portion of the bowl-like inflated balloon projecting in front of the catheter tip, thus preventing contact between the mucous membrane of the urinary bladder and the catheter tip as well as the radial inlet opening.

2. The urinary catheter according to claim 1, wherein reinforcement of a portion of the wall of the expandable balloon remote from the catheter tip is attained by arranging reinforcing ridges on said portion.

3. The urinary catheter according to claim 1, wherein a reinforcement of a portion of the wall of the expandable balloon remote from the catheter tip is attained by making the wall portion thicker than the rest of the balloon.

4. The urinary catheter according to claim 2, wherein the reinforcement of the portion of the wall of the expandable balloon remote from the catheter tip is attained by arranging a tube-like, resilient member over said portion.

* * * * *